United States Patent [19]

Cieutat

[11] 4,372,148
[45] Feb. 8, 1983

[54] GENERATING APPARATUS FOR A VARIABLE FLUID PRESSURE

[76] Inventor: Bertrand G. Cieutat, 2 rue Marie Benaist, 75012 Paris, France

[21] Appl. No.: 192,939
[22] Filed: Oct. 1, 1980
[51] Int. Cl.³ .............................................. G01L 27/00
[52] U.S. Cl. ...................................................... 73/4 R
[58] Field of Search ........................................... 73/4 R

[56] References Cited
FOREIGN PATENT DOCUMENTS 266299  1/1969  U.S.S.R. .............................. 73/4 R Primary Examiner—Kyle L. Howell
Assistant Examiner—Daniel P. Burke
Attorney, Agent, or Firm—Cushman, Darby & Cushman

[57] ABSTRACT

A device for generating a variable frequency, variable pressure in a blood pressure measuring system to test the system for resonance or damping. The device includes within a container an opening for connection to a source of constant pressure, an exit opening where variable pressure is received and an intermediate exhaust opening. Means are provided to partially close the exhaust opening at a variable frequency.

3 Claims, 4 Drawing Figures

GENERATING APPARATUS FOR A VARIABLE FLUID PRESSURE

The present invention relates to a device for generating a variable fluid pressure, those variations in turn having a variable frequency.

Such a device will be particularly used, for instance, in verifying blood pressure measuring devices.

In medical technology and particularly in surgery, it is conventional to have to measure blood pressure, and mainly the variations of this pressure, at the interior of a vessel or of a deep organ.

For such investigations, collectors consisting of flexible tubes or "catheters", of different diameters, thicknesses or lengths, are currently used. Those tubes are filled with a liquid for transmission of pressure, then introduced by an external vessel until a more internal vessel is reached, or to the organ of the patient, the functioning of which is being studied. The free extremity of the catheter is joined to a conventional pressure measuring device having an elastic membrane, where movements of the membrane express the variations of blood pressure at the other extremity inserted in the patient's body. The data on pressure variations are in a very conventional manner shown on a screen, or registered in the form of curves, or even directly treated into electronic data.

But such a transmission system formed by a catheter filled with liquid in relation to an elastic membrane has its own frequency of oscillation, the value of which is entirely uncertain. In fact, it could depend on very numerous factors such as the rigidity of the membrane, the elasticity of the tube, in relation to its thickness, its diameter, its length, or local thickness irregularities; it can still depend on the viscosity of the filling liquid or the presence of air bubbles. The system can then be tuned if frequency of blood pulsation corresponds to its own frequency of oscillation, and the registering curve then appears completely deformed.

Those distortions are even more troublesome as there exists more and more a tendency towards automatic analysis of the variation curves of blood pressure, such analyses taking into account not only the frequency and amplitude of the variations, but also the derivative of those variations, which is the most perturbed size by the parasite phenomena of resonance.

On the contrary, damping phenomena can occur caused, for example, by the presence of blood or air bubbles in the catheter or of the latter's insufficient diameter. Here also, the registering curve is distorted, which nullifies the results of the investigation, especially if the derivative of the recorded curve is taken into account.

It is certain that an experienced practitioner generally will know how to detect, by simple observation of the registering curve, whether it is distorted by a resonance or a damping. But he will not be able to detect the defect after a first measurement, that is, once the catheter is inserted in the vessel or the organ to be explored, and it will be necessary then to withdraw the catheter to change it or cleanse it. This necessitates another introduction, always critical, prolonging by that much the duration of intervention.

Thus it is very important for the practitioner to be able to test the whole measuring system, including the catheter filled with liquid, immediately before introducing it in the vessel of the patient, that is, in the operating room. It is necessary for such a test to submit the system to variable pressures, constant amplitude and at frequencies varying in all the range of frequencies likely to be detected in the patient, and verifying that in this range the system presents neither resonance nor damping.

Devices are presently known for producing such variable pressures in a capacity on which the catheter could be connected before its introduction into the patient's organ.

Such generators are normally formed by a variable frequency electronic simulator, associated to an alternative piston which, by varying the internal volume of a capacity filled with a fluid, varies the pressure with the same frequency. But such devices are cumbersome and complex, and above all are very difficult to sterilize completely and frequently, and it is not easy to put them at the practitioner's disposal even in the operating room.

The present invention allows for the manufacture of a simple and lightweight apparatus, as easily sterilizable as the usual objects utilized in an operating room, and thus likely to be constantly within the range of the practitioner's hand during his intervention.

The invention thus applies to generating apparatus of a variable fluid presssure, with variation frequency varying in a continuous manner, starting from a source of constant pressure fluid pressure, and by utilizing a controlled yield exhaust opening.

According to the invention, the device comprises, in the same container:

a traversing conduit, with an ingress opening for connection to the constant pressure source, an exit opening where variable pressure is received, and an intermediate exhaust opening.

a rotating cam with inertia wheel (turbine) and means for starting rotation, movable means for closing at least partially the exhaust opening, connected to the rotating cam in a manner as to create at least an opening-closing cycle at every turn of the cam.

According to a particular form of embodiment of the invention, the movable closing means of the exhaust opening is formed by a needle mounted elastically on the base of the device, in a manner as to close the exhaust opening, the needle being supported, moreover, on the cam mounted on the axis of the inertia wheel in such a way that, according to the angular positions of the cam in the course of its rotation, the needle will be more or less thrust back thus leaving the exhaust opening more or less open.

According to another particular form of embodiment, the cam is formed by the peripheral part of the inertia wheel, the wheel being disposed in such a manner that its peripheral part is displaced in the immediate neighborhood of the exhaust opening in a manner as to periodically modify the exhaust yield.

The invention also relates to a process for verification of a system for measuring the pressure and variations of the intravascular pressure of an organic liquid, with a view to determining whether the system has proper resonance or damping frequencies in the region of frequencies considered, said measuring system comprising a measuring and so-called registering device connected to a catheter filled with liquid to be introduced into the vessel. According to the invention, the process consists in utilizing the above-described apparatus according to the following process:

Joining the free extremity of the catheter to the exit opening of the traversing conduit, the device having been previously connected to the constant source of pressure;

Starting rotation of the inertia wheel;

Observation for registering pressure variations to the increasing then decreasing frequencies in proportion as the speed is actuated then progressively slowed to the rotation of the wheel, in a manner as to detect the amplitude variations characteristic of possible damping or resonances.

The invention will be better understood by referring to particular embodiments, given as examples and shown by the annexed drawings.

FIGS. 1 and 2 of the sole drawing sheet relate to a device using a closing needle on the exit opening;

Figure 3:
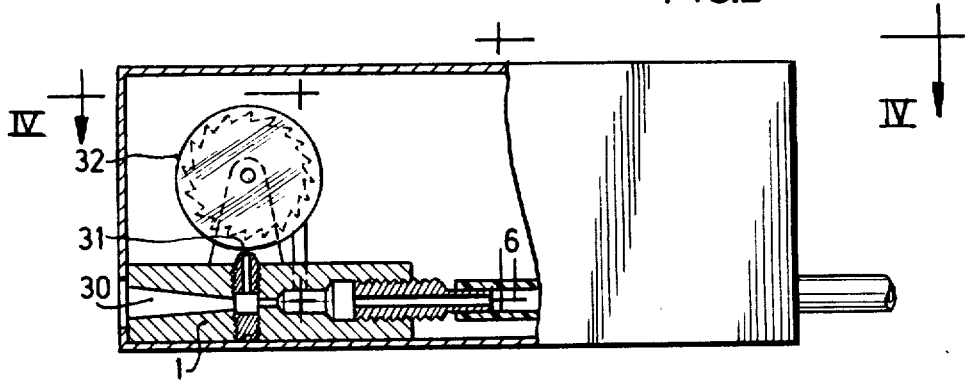
Figure 4:
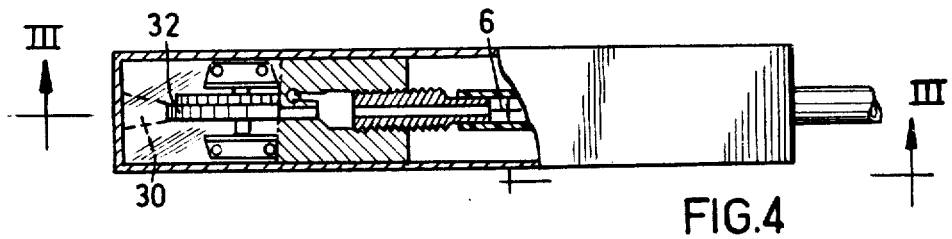

FIGS. 3 and 4 relate to a device using the wheel per se as closing cam for the exit opening.

FIG. 3 is a cross-sectional view according to IV—IV.

FIG. 4 is a view from above, the container being supposedly lifted up and the device partially cut according to III—III.

By referring to the aggregate of the figures, it will be seen that the apparatus is formed of a block pierced by different openings or threadings serving as support for the floor of the wheel and mounted in a closed container of a nonspecific form in the present case.

The block 1 is perforated by a conical boring hole 2 (serving to connect the catheter) the small diameter extremity of which communicates on the one hand with the controlled outlet tube 3 and on the other hand, with the constant outlet tube 4.

The other extremity of the constant outlet tube 4 communicates with a conduit 5 connected to the constant pressure fluid source 6. This same conduit 5 communicates with an outlet tube 7 disposed in such a way that it directs a jet of gas on the paddle-boards of the turbine 14.

It is easily understood that pressure in the conical boring hole 2 (when it is obstructed by the catheter in which pressure is desired to be generated) depends upon the pressure prevailing in conduit 5 on the one hand, and the relationship of the exit resistances of the outlet tubes 3 and 4 on the other hand. The exit resistance of the outlet tube 4 is constant while that of the outlet tube 3 varies between infinity (outlet tube hermetically closed) and the value determined by the fully opened outlet tube itself.

Intermediate values depend upon the more or less great obstruction of the exit 3.

This exit 3 is obstructed more or less by a needle 10 in a form appropriate to the law of variation of the desired pressure integral of the elastic stem 11 fixed at 12 on the base. The elastic stem 11 is maintained by its own elasticity in light contact with the cam 13 integral with turbine 14 equipped with paddle-boards 15 at its periphery, turning in the axis 16 mounted on supports 17 and 18. Rotation of cam 13 will cause stem 11 to effect a come and go movement according to a law of variation depending on the proper form of the cam. It will be easy particularly to obtain a very sensibly alternative and sinusoidal movement by using a cam formed by a simple eccentric disc.

In a rest position, the wheel 14 is immobilized by a blade 20 integral with a second flexible blade 21, fixed by one extremity at 22 at the interior of the container, for example. The other extremity 23 carries a button protruding at the exterior of container 24. It is understood that pressure on the button 24 will cause the flexible blade 21 to bend and will remove blade 20 from the wheel 14 freeing it.

If a certain fluid pressure is applied simultaneously in the conduit 5 by means of pipe 6 connected to the source of pressure, the outlet tube 7 disposed tangentially to the wheel 14 will act to make it turn by action on the paddles 15. Starting rotation of the wheel thus is effected simply by liberating it by pressure on button 24.

The great simplicity of construction and utilization of the device thus made should be noted, and this permits such an accessory to be within the range of the surgeon in the operating room after sterilization by conventional means.

When the practitioner is ready to effect an intravascular blood pressure measurement, the measuring and registering device is connected to a catheter filled with liquid, like physiologic serum. In order to verify the aggregate of the measuring system, before introducing the catheter in the patient's blood vessel, it is sufficient to connect the extremity of the catheter into the opening 2 of the device which will have been, previously, connected by opening 6 to a stable pressure source of compressed gas, air or oxygen for instance, usually available in an operating room.

The conical form of the opening 2 allows for the connection without previous adjustment of the catheters having different diameters. The button 24 is then pressed, which has the effect of liberating wheel 14 which will then be carried away in rotation by the jet of fluid coming from outlet tube 7. The wheel 14 integral with cam 13 will cause alternative displacement of needle 10. The periodic variation of the exhaust section of outlet tube 3 causes a periodic pressure variation in opening 2. The catheter and measuring device are thus subjected to constant amplitude variable pressures, the frequency of variation of which increases during actuation of the wheel, then decreases when the wheel is braked by releasing the button.

A range of frequency larger than that which can be observed by the patient will be covered, and if the test of registration obtained with the pressure generating device does not show disturbances caused by a resonance or a damping, the catheter can be introduced in the patient's vessel without the risk of there appearing such disturbances later.

Figure 1:
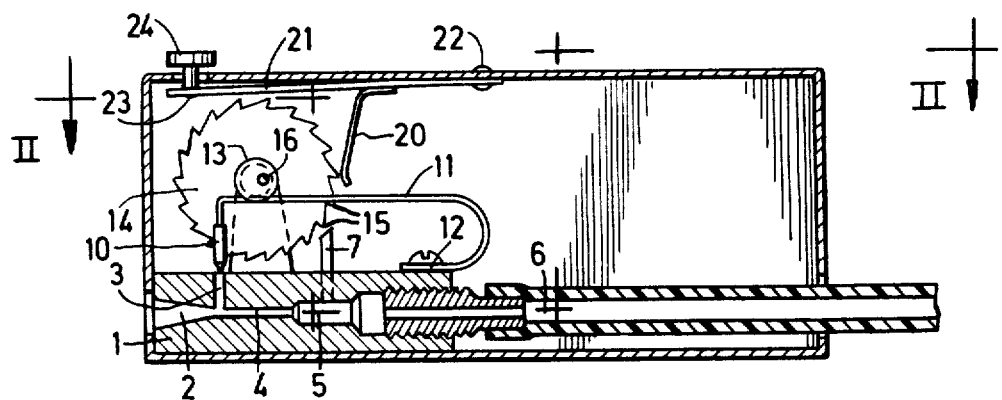
FIG. 1 is a cross-sectional view of the device according to I—I.
Figure 2:
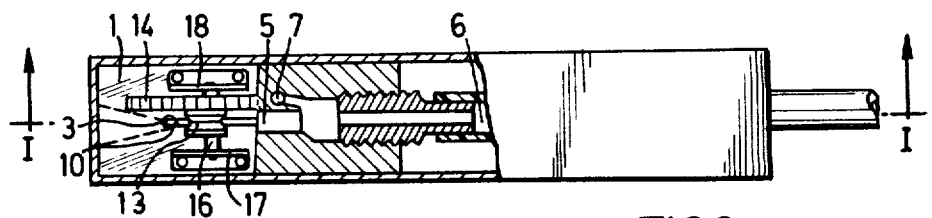
FIG. 2 is a view from above, the container being supposedly lifted up and the device partially cut according to II—II.

The device described at FIGS. 3 and 4 is a variation of an embodiment which is used in the same manner as that of FIGS. 1 and 2. But, here, the support block is perforated in a different manner, so that the conical exit opening 30 communicates with the outlet tube 31 which opens in the immediate proximity of the periphery of wheel 32. The smooth periphery of wheel 32 passes in the immediate proximity of outlet tube 31; thus, when the wheel is turning, its periphery alternately gets farther or closer to the opening 31 by periodically varying the outlet yield, and by varying with the same frequency the pressure in opening 30 where the catheter will be connected. An eccentric circular wheel will produce a pressure variation according to an alternative practically sinusoidal law but one could naturally imagine other forms of wheel producing different laws of variations.

Of course, the invention is not strictly limited to the embodiments which have been described as an example, but it also covers the embodiments which would differ from it only in details, by the variations carried out or by the use of equivalent means. Thus it is that any other system could be used to start the wheel in rotation, for example a simple hand launching by acting on the protruding part, or else launching by any spring, electric motor or other system.

The invention can be applied under the same conditions to verifications on all transportation systems for fluids capable of presenting resonance or toning down phenomena. Of course the dimensions, frequencies and pressures engendered will be adapted to the system.

What is claimed is:

1. Apparatus for generating a pulsating fluid pressure, the pulsation frequency itself being variable in a continuous manner, comprising:
    a supporting structure; a conduit supported by said structure, with an ingress perforation for connecting a source of fluid under constant pressure thereto, an exit perforation continuously connected to said conduit where the pulsating fluid pressure exits, and an intermediate outlet perforation in said conduit between said ingress and exit perforations,
    a rotating cam with an inertia wheel, and means for launching rotation, and
    movable means for at least partially closing the outlet perforation, operatively connected to said rotating cam in a manner so as to create at least an opening-closing cycle of said closing means at each turn of the cam.

2. Apparatus according to claim 1 wherein the movable closing means is formed by a needle and including means mounting the needle to urge it to open position, said mounting means being engaged with the cam in such a way that, according to the angular positions of the cam in the course of its rotation, the needle will be moved toward and away from the outlet perforation.

3. Apparatus according to claim 1, characterized by the fact that the cam is formed by the peripheral part of the wheel which part forms the movable closing means, the wheel being disposed in such a way that its peripheral part is displaced in the immediate neighborhood of the outlet perforation in a manner as to periodically modify the effective flow area thereof.0000

* * * * *